United States Patent [19]

Steiner et al.

[11] 4,340,369
[45] Jul. 20, 1982

[54] DENTAL ARTICULATING PAPER FORCEPS

[76] Inventors: Artur Steiner, Postfach 65, 7707 Engen, Hegau, Fed. Rep. of Germany; Howard G. Frank, 70 E. 10th St., New York, N.Y. 10003

[21] Appl. No.: 196,741

[22] Filed: Oct. 14, 1980

Related U.S. Application Data

[63] Continuation of Ser. No. 938,758, Sep. 1, 1978, abandoned.

[30] Foreign Application Priority Data

Sep. 1, 1977 [DE] Fed. Rep. of Germany ... 7727100[U]

[51] Int. Cl.³ .............................................. A61C 3/00
[52] U.S. Cl. .................................... 433/162; 128/354
[58] Field of Search ................ 433/162; 128/354, 321; 81/43

[56] References Cited

U.S. PATENT DOCUMENTS

| 1,958,667 | 5/1934 | Howe | 433/162 |
| 2,305,156 | 12/1942 | Grubel | 128/321 |
| 2,796,065 | 6/1957 | Kapp | 128/321 |
| 3,774,306 | 11/1973 | Dobyns | 433/162 |

FOREIGN PATENT DOCUMENTS

| 119234 | 6/1929 | Fed. Rep. of Germany | 433/162 |
| 667040 | 1/1937 | Fed. Rep. of Germany | 433/162 |
| 198521 | 7/1966 | U.S.S.R. | 433/162 |

OTHER PUBLICATIONS

"Silverman's" catoloque, 1976, Miller Articulating Paper Forcep, p. 74.

Primary Examiner—Gene Mancene
Assistant Examiner—John J. Wilson
Attorney, Agent, or Firm—S. C. Yuter

[57] ABSTRACT

A dental articulating forceps has a pair of opposed long thin jaws extending from and offset from interconnected spring arms. The face of one jaw directed toward the other jaw has a central groove of determined shape extending therealong, and the other jaw has a matching elongated projection adapted to be received by the groove.

6 Claims, 10 Drawing Figures

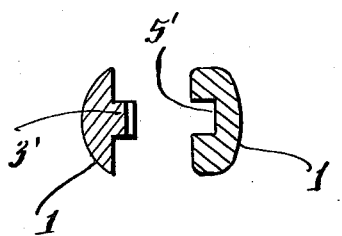
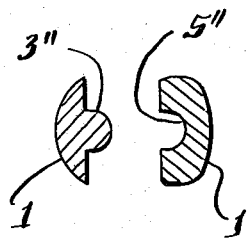
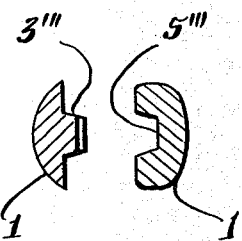
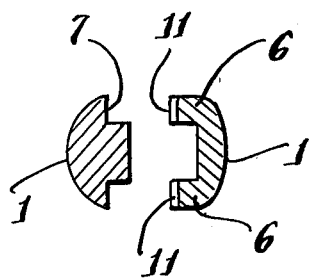
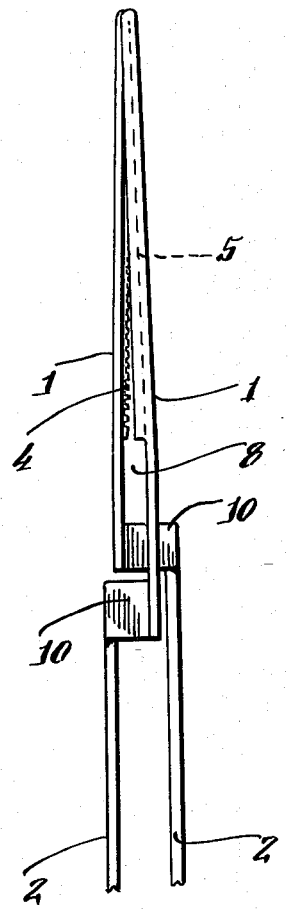

DENTAL ARTICULATING PAPER FORCEPS

This is a continuation of application Ser. No. 938,758, filed Sept. 1, 1978, now abandoned.

BACKGROUND OF THE INVENTION

This invention is related to dental articulating paper forceps, and more in particular to the provision of forceps of this type wherein the jaws are shaped to provide a more firm hold on articulating paper introduced therebetween.

Articulating paper forceps of different types, for use by dentists in the introduction of articulating paper into a patient's mouth, are well known. One type of such forceps includes a pair of spring arms interconnected to each other at one end, and having intermediate arms extending at right angles from their free ends. The spring arms are of different lengths, so that the intermediate arms may cross over relative to one another, and be connected to elongated jaws extending generally parallel to and offset from the arms. The spring action of the arms normally holds the jaws in contact with one another, and this contact may thereby be released, to enable the insertion of paper between the jaws by forcing the ends of the arms together.

Some articulating paper forceps of this type were provided with matching longitudinal serrations for more firmly holding the articulating paper. Other types of such forceps have transversely extending serrations for the same purpose. In the past, however, such expedients did not enable a sufficiently tight grasp on the articulating paper, so that the paper, when bit upon by a patient, moved too freely, thereby resulting in the production of useless, incorrect imprints. This problem was enhanced by the fact that the jaws of some forceps were quite narrow and it was hence not feasible to provide them with adequate stiffness to enable a full and even closing thereof over their entire length.

BRIEF SUMMARY OF THE INVENTION

The present invention is therefore directed to the provision of articulating paper forceps which overcome the above disadvantages of known forceps, in a simple manner, thereby to enable the forceps to hold articulating paper more firmly.

Briefly stated, in accordance with the invention, an articulating paper forceps of the above type is provided wherein the inner face of one of the jaws is provided with a central groove, having a cross section with at least two substantially sharp corners, extending longitudinally therein for substantially the entire length of the jaw. The inner surface of the other jaw is provided with a matching projection adapted to be received by the groove, the projection also preferably extending for substantially the entire length of the jaw. By the use of this expedient, it has been found that the jaws are stiffer than has heretofore been possible, and that the interlocking groove and projection with at least two mated pairs of sharp corners provide a much firmer hold upon the articulating paper.

In variations of the forceps of the invention, the groove and matching projection may have rectangular cross sections, square cross sections, rounded cross sections or trapezoidal cross sections, as an example only. In addition, serrations may be provided to extend laterally across the projection, to enable a still firmer hold on the articulated paper. Alternatively, the lateral or transverse serrations may be provided on the other jaw, on the surfaces thereof adjacent the longitudinally extending groove.

The jaws of the forceps, in accordance with the invention, also have jaws with widths and thicknesses sufficiently great that a high spring force may be operative thereon to enable the jaws to fully and firmly engage one another, in the closed condition, throughout their extent.

BRIEF DESCRIPTION OF THE FIGURES

In order that the invention will be more clearly understood, it will not be disclosed in greater detail, with reference to the accompanying Figures, wherein:

FIGS. 6, 7 and 8 show alternative cross sections of the jaws of FIG. 2, having square, rounded and trapezoidal shaped grooves and projections, respectively;

FIG. 9 shows a further modification of the cross section of the jaws of FIG. 2, wherein the serrations are provided laterally on the jaw face adjacent the longitudinal groove; and FIG. 10 is a top view of a portion of the forceps of FIG. 1, showing the jaws thereof in partially open condition.

DETAILED DISCLOSURE OF THE INVENTION

Figure 2:
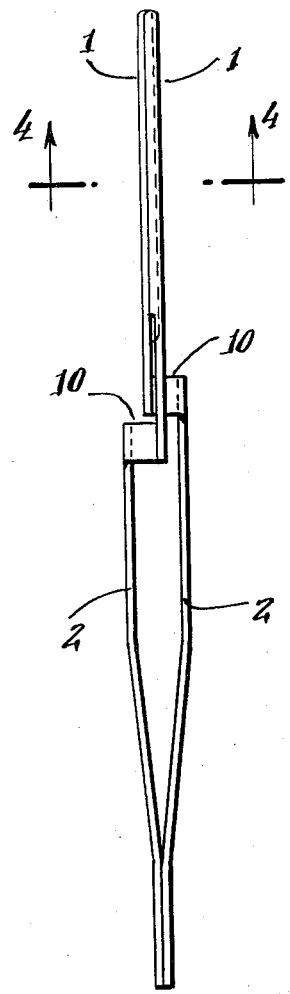
FIG. 2 is a top view of the forceps of FIG. 1.
Figure 1:
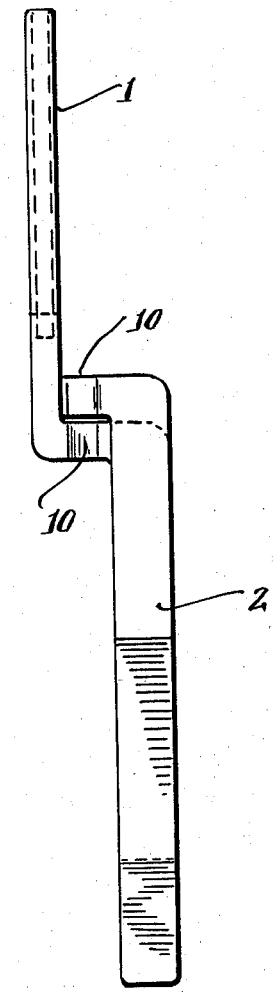
FIG. 1 is a side view of a dental articulating paper forceps in accordance with the preferred embodiment of the invention.

Referring now to the drawings, and more in particular to FIGS. 1 and 2, therein is illustrated a dental articulating paper forceps in accordance with the preferred embodiment of the invention. As is apparent in these figures, the forceps are comprised of a pair of opposed jaws 1 extending from the free ends of a pair of interconnected arms 2. As is more apparent in FIG. 2, the arms are connected together at one end in a tweezer-like manner, so that they are resiliently spread apart at the other end thereof. The arms 2 are of different lengths, and have intermediate arms 10 depending from their free ends, the intermediate arms 10 crossing over one another and being connected to the jaws 1. As a consequence, the jaws extend generally parallel, in the closed condition, to the arms 2, with the spring forces of the arms 2 normally holding the jaws in engagement with one another. The jaws 1, arms 2 and intermediate arms 10 are preferably formed of a resilient material such as spring stainless steel, as is conventional for such dental implements.

Figure 3:
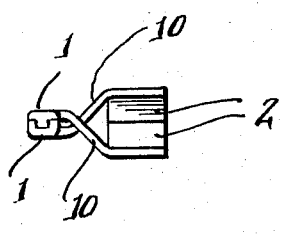
FIG. 3 is an end view of the articulating forceps of FIG. 1, as seen from the ends of the jaws thereof.
Figure 4:
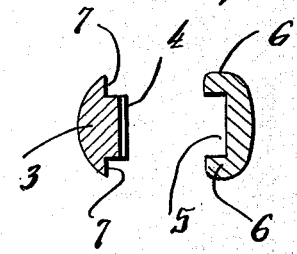
FIG. 4 is a cross-sectional view of the jaws of the forceps, taken along the line 4—4 of FIG. 2.

As more clearly shown in FIG. 4, one of the jaws is provided with a longitudinally extending projection 3 on its inner side, i.e., the side facing the other jaw. The projection 3, which has a rectangular cross section in this embodiment of the invention, extends for substantially the entire length of the jaw from the free end thereof. The projection 3 is centered on the jaw so that the inner face also has narrow flat side edges 7. The inner surface of the other jaw is provided with a longitudinally extending groove 5 of a shape to match the projection or center ridge 3. As a consequence, when the jaws are closed, the groove 5 closely receives the projection 3, and any thin paper (not shown) introduced therebetween. The remaining portions 6 at the edges of the inner face of the jaw having the groove 5 are flat and are positioned to engage the surfaces 7 when the jaws are closed.

It will of course be apparent that the groove and projection or center ridge of the jaws might have other matching shapes. For example, as illustrated in FIG. 6, the center ridge 3' and corresponding groove 5' may be square. Alternatively, as shown in FIG. 7, the center ridge 3'' and the groove 5'' may be rounded. In still another embodiment of the invention, as shown in FIG. 8, the center ridge 3''' and the groove 5''' may be trapezoidal. It will of course be apparent that the center ridge and matching groove may have other transverse cross-sectional surfaces with at least two matched pairs of sharp corners.

Figure 5:
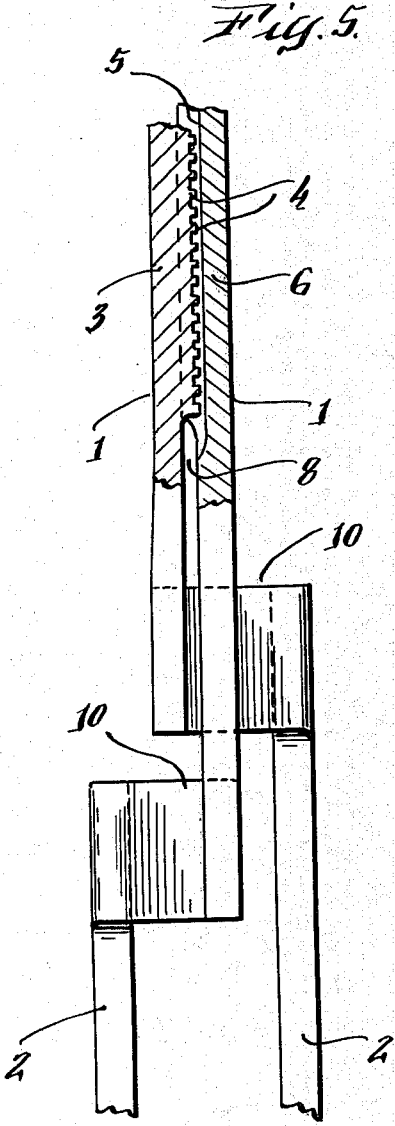
FIG. 5 is an enlarged partially cross-sectional view of the midportion of the forceps of the invention of FIG. 2.

In the modification of the invention more clearly seen in FIGS. 4 and 5, the inner face of the center ridge or projection 3 is provided with laterally, i.e., transversely, extending serrations 4 throughout its length. It has been found that these serrations enable the forceps in accordance with the invention to even more firmly grasp and hold the articulating paper. In the modification thereof, as illustrated in FIG. 9, the transverse or lateral serrations are provided on the side edges 6, instead of on the center ridge 3, for the same purpose.

In the closed condition of the jaws, the serrations 4 engage the bottom of groove 5, in the arrangement of FIG. 4. Similarly, in the arrangement of FIG. 9, in the closed condition the serrations 11 meet and engage the surfaces 7.

Simultaneously, in each case, the remaining facing parts of the jaw engage each other firmly in the closed condition of the jaws.

While the center ridge 3 and groove 5 may extend coextensively with the jaws throughout their entire length, in the embodiment of the invention illustrated in FIGS. 2 and 5, the center ridge and groove do not extend completely to the intermediate arms 10, and the jaws are cut out as illustrated at 8, in a short region. In other words, the center ridge 3 may be completely absent in this region 8, with the inner face of the other jaw being cut so that it is substantially at the level of the bottom of the groove 5. This portion of the jaws is preferably relieved to such an extent that if the inner faces thereof do ever contact one another, it is only when a firm and tight contact is established between the portions of the length of the jaws which have the ridge and groove. This feature also enables the jaws to hold the articulating paper more secure, not allowing it to move. The grooved and ridged inner faces of the jaws do extend, however, completely to the free ends of the jaws.

As above discussed, the forceps in accordance with the invention are normally closed and held in the closed condition by the spring forces of the arms 2. Consequently, the jaws may be opened by the application of pressure between the ends of the arms 2, by the fingers of the operator. Upon releasing of this pressure, to close the jaws, the jaws initially engage each other only at the free ends thereof, as illustrated in FIG. 10. Upon further releasing of the arms 2, the area of contact between the jaws gradually increases toward the arms, until the full contact is achieved as illustrated in FIG. 2. The arms and intermediate arms of the forceps are consequently shaped to enable the initial contact between the jaws as shown in FIG. 10. It is further apparent that the spring tension of the forceps is selected to achieve a closing of the above described nature, so that the relatively long jaws may close tightly and forcefully against each other, for securely holding the articulating paper and not permitting it to move.

FIGS. 1 and 2 of the drawings generally show the relative proportions of the different parts of the forceps of the invention, in accordance with a preferred embodiment thereof. In this embodiment of the invention the grooved and ridged portions of the jaws have lengths of about 47 mm, the overall length of the forceps being about 15.6 centimeters.

While the invention has been disclosed and described with reference to a limited number of embodiments, it will be apparent that variations and modifications may be made therein, and it is intended in the following claims to cover each such variation and modification as falls within the true spirit and scope of the invention.

What is claimed is:

1. In dental articulating paper forceps having a pair of aligned elongated jaws extending from interconnected spring arms and movable toward and away from one another with said spring arms resiliently holding said jaws together, said spring arms being the sole means holding said jaws together, the improvement where one of said jaws has a central ridge laterally recessed from the sides of the jaw and extending longitudinally substantially throughout its length and facing the other jaw, and the other of said jaws has a central longitudinally extending recess of a cross section matching said ridge and positioned to receive said ridge upon closure of said jaws, said central ridge having a cross secton with four substantially sharp corners and also having lateral serrations extending thereacross thoughout its length, each of said four substantially sharp corners of said central ridge abutting a mating substantially sharp corner of said central longitudinally extending recess so that when said spring arms are resiliently and solely holding said jaws together each of said four mated pairs of sharp corners is adapted to tightly engage thin dental articulating paper, whereby thin dental articulating paper when bit upon by a patient does not move between said jaws.

2. The dental articulating paper forceps of claim 1 wherein said central ridge is relieved in a relatively short portion of said one jaw adjacent the respective arm, and the sides of the recess of the other jaw are relieved in the same region adjacent the respective arm, whereby the recessed and ridged portions of the jaws fully contact one another throughout their extent upon closure of the jaws, before any contact can be made between the portions of the jaws joining said arms.

3. The dental articulating paper forceps of claim 2 wherein said jaws are offset from said arms, and extend substantially parallel thereto, said jaws being joined to said arms by intermediate arms that cross over one another.

4. The dental articulating paper forceps of claim 1 wherein said ridge and groove have substantially rectangular transverse cross sections.

5. The dental articulating paper forceps of claim 1 wherein said ridge and groove have substantially square transverse cross sections.

6. The dental articulating paper forceps of claim 1 wherein said ridge and groove have substantially trapezoidal transverse cross sections.

* * * * *